United States Patent [19]

Heynen et al.

[11] Patent Number: 5,347,023
[45] Date of Patent: Sep. 13, 1994

[54] PROCESS FOR TREATING FATTY ACIDS

[75] Inventors: Antonius J. M. Heynen, Walbecklaan; James P. Ward, Vlaardingen, both of Netherlands

[73] Assignee: Unilever Patent Holdings B.V., Rotterdam, Netherlands

[21] Appl. No.: 13,535

[22] Filed: Jan. 28, 1993

Related U.S. Application Data

[63] Continuation of Ser. No. 574,350, Aug. 29, 1990, abandoned.

[30] Foreign Application Priority Data

Aug. 29, 1989 [NL] Netherlands .......................... 8902182

[51] Int. Cl.$^5$ .............................................. C11B 3/02
[52] U.S. Cl. ................................... 554/186; 554/175; 554/184; 554/185
[58] Field of Search .......................... 554/170, 185, 186

[56] References Cited

U.S. PATENT DOCUMENTS 4,371,469 2/1983 Foglia et al. ..................... 260/413 R

OTHER PUBLICATIONS

Fukuhara, Chemical Abstracts, vol. 108, #8, p. 121, 1988, 58327b.
Streitwieser et al. *Intro to Organic Chemistry*, 2 ed. 1981, Chap. 18 "Carboxylic Acids" p. 516.

*Primary Examiner*—José G. Dees
*Assistant Examiner*—Deborah D. Carr
*Attorney, Agent, or Firm*—Cushman, Darby & Cushman

[57] ABSTRACT

A mixture of branched fatty acids containing 18 carbon atoms such as commercial iso-stearic acid is treated to lower the freezing point to below −10° C., by mixing with urea and a lower alcohol, such as methanol, and filtering. The product is useful in the production of low freezing point esters for use as lubricants.

6 Claims, 1 Drawing Sheet

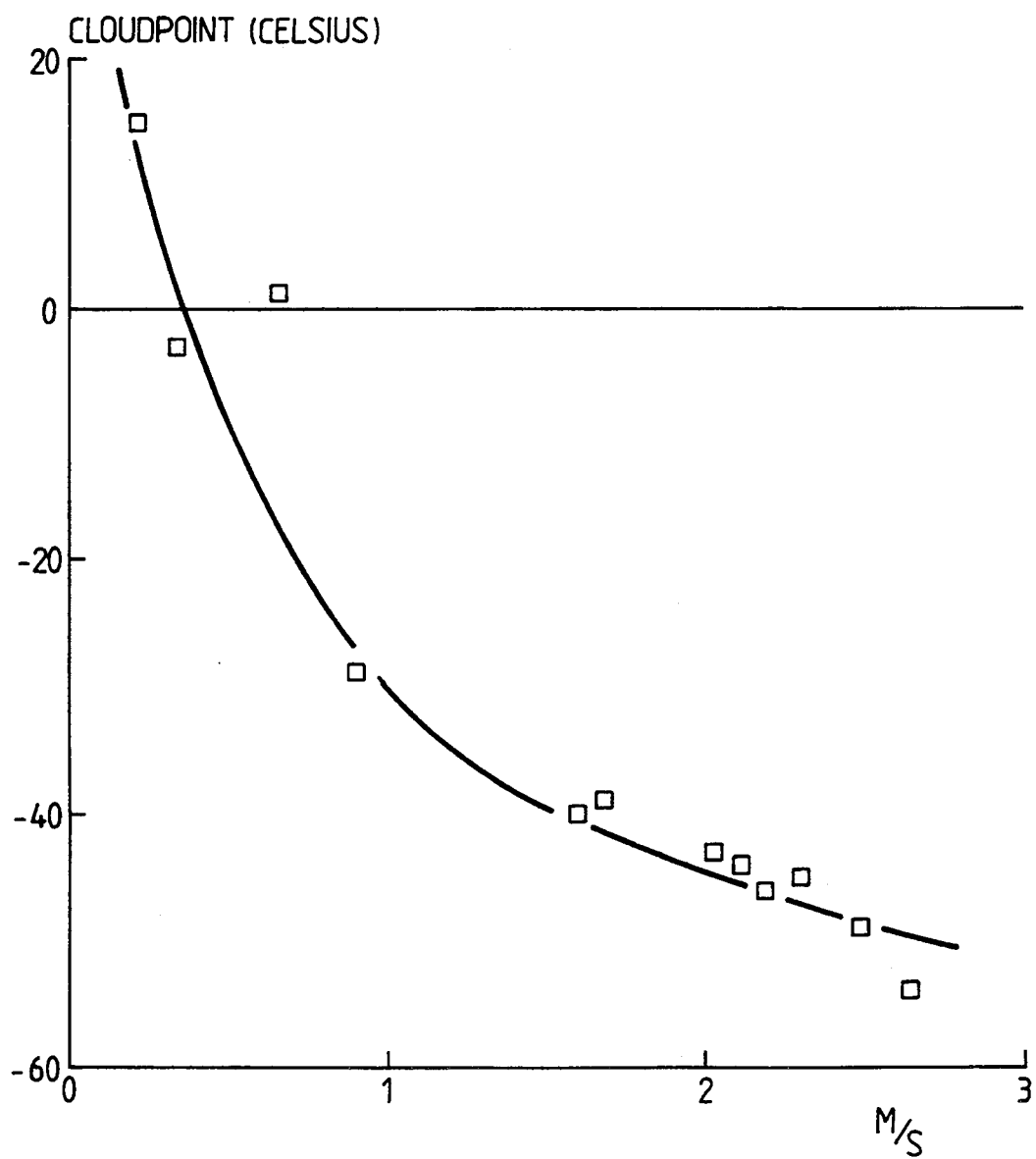

PROCESS FOR TREATING FATTY ACIDS

This is a continuation of application Ser. No. 07/574,350, filed on Aug. 29, 1990, abandoned.

The present invention relates to a process for treating fatty acids by mixing the starting material with urea and a lower alcohol, filtering the mixture and purifying the filtrate. The invention also relates to a process for the preparation of an ester with a low freezing point from an alcohol and a fatty acid.

The use of urea for treating fatty acids is known from various publications. For example, European Patent Specification No. EP-A-178,422 (Nestle) describes a process for the selective concentration of polyunsaturated fatty acids whose first double bond is in position 6 from a mixture of polyunsaturated fatty acids whose first double bond is variously in position 6 and in position 9 and treating the starting mixture with a solution of urea in a lower alcohol. The required linolenic acid with a higher ratio of the form with the double bond in position 6 is then isolated from the filtrate.

Japanese Patent Application No. JP 84/206,870 (KANEBO) describes a process for the preparation of a urea inclusion compound of azelaic acid [COOH. $(CH_2)_7COOH$] by mixing a warm aqueous solution of urea with a methanolic solution of azelaic acid, with stirring, followed by cooling. The resulting inclusion compound is a white powder that is used as a cosmetic for cleansing the skin.

Japanese Patent Application No. JP 76/156,255 (ASAHI) corresponding to Japanese Kokai 78/82,718, describes a process for purifying unsaturated fatty acids and their esters by mixing notably decane-1, 10-dicarboxylic acid and its diethyl ester with a methanolic solution of urea at 50° C. and then allowing the mixture to stand at 20° C. for 3 h, during which time an inclusion compound precipitates out, giving the required product in a purity of 99.5%.

A. Aarna, J. Kann and J. Mannik have published an article entitled "Use of urea inclusion compounds of dimethyl esters of aliphatic dicarboxylic acids" in the Soviet publication Trudy Tallin. Politekh. Inst., Seriya A, No. 254, (1967) pp. 3–12, which describes a method for the preparation of urea inclusion compounds of the dimethyl esters of $C_4$–$C_{10}$ aliphatic dicarboxylic acids, where the inclusion depends on the chain length of the dicarboxylic acid.

Czechoslovak Patent Application No. CS 76/4064 (KUFNER J) describes a process for the preparation of a urea inclusion compound of a fatty acid by mixing the fatty acid and urea as solids in a mill at a temperature of 40°–50° C. The fatty acids used may be either saturated or unsaturated, and they may contain 10–27 carbon atoms. The resulting inclusion compound is used as a food additive.

German Patent Specification No. DE-A-1,932,919 (ESSO) describes a process for separating hydrocarbon mixtures under anhydrous conditions with the aid of thiourea. This process can be used for example for dewaxing a fuel and improving the pour point of the resulting lubricating oil fraction.

Indian Patent Specification No. IN 145,921 (UNILEVER) describes a process for the preparation of urea inclusion complexes of fatty acids, the resulting inclusion compounds being used for preparing soap bars.

German Patent Specification No. DE-A-2,627,459 (UNILEVER) also describes a process for the preparation of inclusion compounds from urea and a fatty acid in order to obtain a detergent, and specifically soap in tablet form.

German Patent Specification No. DE-A-2,264,226 (RALSTON PURINA) describes a process for the preparation of an animal feedstuff for ruminants, comprising inclusion compounds of a fatty acid and urea by using a warm aqueous solution of urea and fatty acids derived from acidified soap material and hydrolysed fish oil.

There is a need for lubricants based on a fatty acid esters that remain liquid at low temperatures of e.g. below −10° C. Investigations have shown that it is best to prepare such an ester from a fatty acid that itself has a low freezing point i.e. the temperature upon cooling at which visible crystals are formed. This can be done by using a fatty acid with a low number of carbon atoms and/or by using branched fatty acids i.e. fatty acids in the iso- form. However, an ester of a fatty acid with a low number of carbon atoms has a low lubricating action.

For example, stearic acid, which contains 18 carbon atoms, has a melting point of 69.9° C, while caprylic acid, which contains eight carbon atoms, has a melting point of 16.5° C. Butyric acid contains four carbon atoms and has a melting point of −4.7° C., while isovaleric acid contains five carbon atoms and has a melting point of −51° C. Commercial forms of "isostearic acid", which predominantly contains 18 carbon atoms and is generally a mixture of branched fatty acid isomers, has a melting point of about 5° C., with variations according to the isomer composition.

It has been found desirable to prepare a lubricant from isostearic acid.

It has now been found possible to obtain a fatty acid mixture having a relatively low melting or freezing point by using the process of the present invention. As mentioned in the introduction, this process is characterised in that the starting material essentially comprises a mixture of branched fatty acids predominantly containing 18 carbon atoms, and in that a fraction with a reduced freezing point below −10° C. is isolated from the filtrate.

It has now been found possible, surprisingly, to take a commercial isostearic acid isomer and treat it by a simple process to obtain a product that meets the requirement in question, i.e. to obtain a product that has a low freezing point.

Publications dealing with the treatment of fatty acids with urea, carried out to obtain inclusion compounds, indicate that it is possible to separate in this way saturated fatty acids from unsaturated ones, or to separate various fatty acids having different chain lengths from one another. However, they do not describe a way to separate the various isomers of commercial isostearic acids according to their degree of branching and to their position of branching, and so to prepare a fatty acid with a reduced freezing point.

Now that it has been found possible to prepare a fatty acid with a greatly reduced freezing point, it has also become possible to prepare from this fatty acid the required lubricants or esters that remain liquid at the low temperatures of even below e.g. −50° C. The preparation of esters from these fatty acids is itself common knowledge well known to one skilled in the art.

The process according to the invention may be carried out in the following manner. The mixture of branched chain fatty acids such as commercial isostearic acid are dissolved in urea and a lower alcohol, for example by warming to a temperature of at least 60° C. under refluxing conditions. The weight ratio of the fatty acids to the urea may be from 4:1 to 1:4, preferably from 1:2 to 1:4. The lower alcohol preferably has from 1 to 4 carbon atoms, and ideally is methanol or ethanol because of their relative ease of subsequent removal. In order to reduce esterification of the alcohol during the process, some water may be present in the alcohol, such as from 5 to 15%, based on the weight of the alcohol. The weight ratio of urea to the aqueous alcohol is preferably from 1:1 to 1:4.

Once the clear solution has formed, it should be cooled to room temperature or below to cause the urea inclusion compound to crystallise out. The crystals may be separated by filtering or by any equivalent method such as centrifugation. The residue may be rejected, but if desired it is possible to extract a different fatty acid fraction therefrom, having a higher freezing point than the starting material. This is achieved by dissolving the crystals in warm mineral acid and then allowing the fatty acid fraction to separate such as in a separating funnel, whereafter it may be washed with water to remove traces of alcohol and acid, and then dried.

The filtrate however contains the fatty acid fraction with the lower freezing point and this may be isolated from the alcohol, any water and unreacted urea by suitable means, such as by evaporating the lower alcohol, by distillation or alternatively by neutralising the urea with concentrated aqueous mineral acid, for example hydrochloric acid, and extracting the fatty acids with a solvent, such as hexane, which is then removed by evaporation.

Having obtained the fatty acid fraction with the lower freezing point in this one step, it is possible to subject this fraction to another such process to still further reduce the freezing point. In this case it is advisable to carry out each step with a fatty acid to urea weight of from 2:1 to 1:2.

The following Examples serve to illustrate the process of the present invention as regards the preparation of branched fatty acid mixtures with a low freezing point.

All the analyses were carried out by gas chromatography.

EXAMPLE 1

One hundred grams of commercial isostearic acid and 300 g of urea were dissolved in a known amount of methanol by gentle warming to 68° C. under refluxing conditions. The isostearic acid used was a commercial product marketed by Unichema International under the trade name of Prisorine 3505, which is a mixture of branched fatty acid isomers. The methanol contained 10wt% of water (calculated on the amount of methanol itself) in order to prevent the formation of methyl isostearate. The solvent in fact consisted of 545 g of methanol and 55 g of water.

When the urea had dissolved, as indicated by the formation of a clear solution, the mixture was cooled to room temperature. As a result, urea crystallised out of the supersaturated solution, part of the isostearic acid being incorporated in the crystal structure of urea. The crop of crystals was filtered off, the filtrate was collected, the volatile compounds were distilled off from it, and the dissolved urea was removed by washing with acidified warm water. The material obtained here was purified by distillation, and the freezing point was determined on the purified product.

Analysis gave the following figures. The filtrate contained 55wt% of the starting material. The freezing point of Prisorine is 1° C. The freezing point of the fatty acid fraction obtained from the urea inclusion compound was 26° C., while the fraction obtained from the filtrate was −54° C. This illustrates the surprisingly efficient lowering of the freezing point of the fatty acid fraction prepared by the process of the present invention.

Table 1 shows the composition of the starting material and the two fractions obtained.

TABLE 1

Composition (%) and freezing point of the fatty acid product containing isostearic acid, obtained in Example 1

|  | $<C_{16}$ acids | Palmitic acid | Branched $C_{18}$ fatty acids |
|---|---|---|---|
| Starting material (Prisorine) | 4.8 | 5.0 | 71.8 |
| Main product (from the filtrate) | 11.8 | 1.3 | 63.7 |

|  | Stearic acid | $>C_{18}$ acids | Freezing point |
|---|---|---|---|
| Starting material (Prisorine) | 1.6 | 16.7 | +1° C. |
| Main product (from the filtrate) | 1.0 | 22.2 | −54° C. |

EXAMPLE 2

The process used in Example 1 was repeated with 7000 g of Prisorine 3505 and 7000 g of urea, dissolved in 12,700 g of methanol and 1300 g of water. The filtrate contained 70 of the starting material. The fatty acid fraction obtained from the filtrate had a freezing point of −29° C. The composition of the main product is shown in Table 2.

EXAMPLE 3

Using the product obtained from the filtrate in Example 2, 1800 g of isostearic acid were mixed with 1800 g of urea and 3600 g of methanol, containing 10 wt% of water, to subject the product obtained in Example 2 to a second stage of processing. The filtrate was again found to contain 70% of the starting material. The freezing point of the fatty acid fraction obtained from the filtrate was −39° C. while the freezing point of the fraction obtained from the inclusion compound was 4° C. The other data are listed in Table 2.

TABLE 2

Composition (%) and freezing point of the fatty acid products obtained from the filtrate fraction in Examples 2 and 3

|  | $<C_{16}$ acids | Palmitic acid | Branched $C_{18}$ fatty acids |
|---|---|---|---|
| Starting material (Prisorine) | 4.8 | 5.0 | 71.8 |
| Main product (from the filtrate) |  |  |  |
| in Example 2 | 8.1 | 1.0 | 76.6 |
| in Example 3 | 8.7 | 1.1 | 72.5 |

|  | Stearic acid | $>C_{18}$ acids | Freezing point |
|---|---|---|---|
| Starting material (prisorine) | 1.6 | 16.7 | +1° C. |
| Main product (from the filtrate) |  |  |  |
| in Example 2 | 0.7 | 13.6 | −29° C. |

TABLE 2-continued

Composition (%) and freezing point of the fatty acid products obtained from the filtrate fraction in Examples 2 and 3

| | | | |
|---|---|---|---|
| in Example 3 | 0.6 | 17.1 | −39° C. |

EXAMPLE 4

A two-step processing operation was carried out on a semi-technical scale, using 14 kg of Prisorine 3505, 14 kg of urea, 25.2 kg of methanol and 2.8 kg of water. The mixture was heated at 68° C. in a stirred reactor for 30 min, during which time the urea dissolved in the solvent. The mixture was then cooled to 20° C., with slow stirring. The stirring was stopped as soon as the temperature had reached 20° C., whereupon urea crystallised out in the form of an inclusion compound. The mixture was allowed to stand in the reactor overnight, then filtered, and 30 l. of the filtrate were collected for use as the starting material for the final product.

The reactor was cleaned out with hot water, the filtrate was returned to it, and 11 kg of urea were added. The mixture was again heated to 68° C. with stirring and kept at this temperature for 30 min. All the urea having dissolved, the mixture was cooled to 20° C., with slow stirring. The stirring was stopped when this temperature had been reached, and the urea adduct was then allowed to crystallise out. The next day the material in the reactor was filtered, and the filtrate was collected in a container.

This gave about 25 l. of filtrate, from which about 10 l. of aqueous methanol were evaporated off at 71°–72° C., the rest being removed at a reduced pressure of 200 mm Hg. The mixture was then stirred and cooled to 50° C. The material thus obtained was washed with three 25-litre portions of water at a temperature of 99° C., the first portion of water containing 10 wt% of HCl. This operation gave 7 kg of an end product, which was found to have a freezing point of −40° C.

The yield in the first step was 70%, calculated on the amount of starting material containing isostearic acid. Processing the first-stage filtrate also gave a yield of 70% in the second stage, so that the overall yield was about 49%.

The residue obtained in the first and second stage of processing was purified by washing with boiling water, which dissolved the urea crystals, the amount of residue being 30% in both stages. The freezing point of the isostearic acid fraction obtained from the residue was found to be 4° C.

EXAMPLE 5

In order to investigate the possible understanding of the invention, the process of Example 1 was followed except that variations were made in the starting fatty acid mixture, the fatty acid to urea ratio, the choice of methanol or ethanol as the lower alcohol and the number of steps of the process. Thereby a number of products were obtained having different melting points. Each product was analysed, by known gas chromatography methods, for its content of singly-branched and multiply-branched fatty acids.

The results were as set out in the following Table 3, which also includes corresponding results for Examples 1 to 3. M/S indicates the weight ratio of multiply-branched to singly-branched fatty acids.

TABLE 3

| Example No. | M/S | Cloud points (°C.) |
|---|---|---|
| 1 | 2.64 | −54 |
| 5A | 2.49 | −48 |
| 5B | 2.19 | −46 |
| 5C | 2.31 | −45 |
| 5D | 2.11 | −44 |
| 5E | 2.03 | −43 |
| 5F | 1.61 | −40 |
| 3 | 1.69 | −39 |
| 2 | 0.90 | −29 |
| 5G* | 0.34 | −3 |
| 5H* | 0.07 | +4 |
| 5I* | 0.22 | +15 |

*comparative examples:
5G — fatty acid mixture extracted from the inclusion product of Example 5F
5H — ditto from Example 3
5I — ditto from Example 5E

BRIEF DESCRIPTION OF THE DRAWING

The results are plotted in the attached Figure, which shows the variation of the cloud point (freezing point) of the fatty acid mixture against the ratio for the singly-branched to multiply-branched fatty acids in the product.

It will be seen from the Figure that there is clearly a relationship between the freezing point of the fatty acid and its distribution of branching and that by use of the present invention, the multiply-branched to singly-branched ratio may be increased.

Although the invention is not restricted to a given theoretical explanation, it can be assumed on the basis of the results obtained that the low freezing point achieved is due to a certain fraction of branched fatty acid with a certain degree of branching. This certain degree of branching of the isostearic acid is probably more important here than the large amount of compounds containing more than 18 carbon atoms and the small amount of unbranched compounds.

The data listed in Tables 1 and 2 indicate that the results obtained in Example 1 are the best as regards a low freezing point, since this is down to −54° C. there, although the yield is higher in Example 2 than in Example 1. It can also be deduced that the two-stage processing, as described in Example 3, gives a better result than the method used in Example 2, since the freezing point is reduced here to −39° C. by carrying out a two-stage processing operation in which the product obtained in Example 2 having a freezing point of −29° C. is subject to a second processing stage.

We claim:

1. A process for obtaining a fatty acid product having a reduced freezing point below −10° C., as compared to the freezing point of the starting material, which comprises dissolving urea and a fatty acid starting material containing a mixture of single branched and multiple branched fatty acids predominantly containing 18 carbon atoms, in a lower alcohol, cooling the resulting solution so as to crystallize out crystals of a urea inclusion compound, and recovering said fatty acid product from the remaining solution, said recovered fatty acid product having an increased multiple branched to single branched ratio as compared to the multiple branched to single branched ratio of the fatty acid starting material.

2. A process according to claim 1, wherein the material is dissolved in water-containing methanol.

3. A process according to claim 1, wherein the ratio between the weight of the branched fatty acids and that of urea is between 1:4 and 4:1.

4. A process according to claim 1, wherein the material of branched fatty acids is dissolved in the aqueous lower alcohol and mixed with urea at an elevated temperature, and this is then reduced to room temperature or below to cause the urea inclusion compound to precipitate.

5. A process according to claim 1, wherein the product with a reduced freezing point is recovered from the solution by evaporating the aqueous lower alcohol.

6. A process according to claim 1 wherein the fatty acid starting material is isostearic acid.

* * * * *